(12) United States Patent
Kecman et al.

(10) Patent No.: US 8,496,010 B2
(45) Date of Patent: Jul. 30, 2013

(54) SURGICAL INSTRUMENT ATTACHMENT

(75) Inventors: Maja Kecman, London (GB); Lisa Stroux, Heidelberg (DE); Alberto Verteramo, Leeds (GB); Alan Ashby, Leeds (GB)

(73) Assignee: Depuy International Limited (GB)

( * ) Notice: Subject to any disclaimer, the term of this patent is extended or adjusted under 35 U.S.C. 154(b) by 572 days.

(21) Appl. No.: 12/679,018

(22) PCT Filed: Sep. 19, 2008

(86) PCT No.: PCT/GB2008/003182
§ 371 (c)(1),
(2), (4) Date: Mar. 23, 2010

(87) PCT Pub. No.: WO2009/037470
PCT Pub. Date: Mar. 26, 2009

(65) Prior Publication Data
US 2010/0305488 A1    Dec. 2, 2010

(30) Foreign Application Priority Data
Sep. 21, 2007    (GB) .................................. 0718416.1

(51) Int. Cl.
*A61F 5/37*    (2006.01)
(52) U.S. Cl.
USPC ....................................................... 128/882
(58) Field of Classification Search
USPC ................. 602/23, 62; 128/869, 882; 606/53, 606/86 R, 88
See application file for complete search history.

(56) References Cited

U.S. PATENT DOCUMENTS

| | | | |
|---|---|---|---|
| 4,665,904 A * | 5/1987 | Lerman | 602/27 |
| 4,841,975 A | 6/1989 | Woolson | |
| 5,197,944 A | 3/1993 | Steele | |
| 5,628,750 A | 5/1997 | Whitlock et al. | |
| 5,908,424 A * | 6/1999 | Bertin et al. | 606/88 |
| 6,221,035 B1 | 4/2001 | Kana et al. | |
| 2005/0187557 A1 | 8/2005 | Collazo | |
| 2006/0241639 A1 | 10/2006 | Kuczynski et al. | |

FOREIGN PATENT DOCUMENTS

| | | |
|---|---|---|
| EP | 1040791 A1 | 10/2000 |
| EP | 1754457 A2 | 2/2007 |
| EP | 1852072 A2 | 11/2007 |
| WO | WO 2005110249 A1 | 11/2005 |

OTHER PUBLICATIONS

PCT International Search Report and Written Opinion PCT/GB2008/003182 dated Dec. 3, 2008.
UK Search Report 0718416.1dated Dec. 10, 2007.
Millard, T. et al; Tibial Cutting Guide With Adjustment Handgrip; European Patent No. 1040791A1; Oct. 4, 2000; English Abstract; MicroPatent Report; 2010 MicroPatent LLC.

* cited by examiner

*Primary Examiner* — Patricia Bianco
*Assistant Examiner* — Camtu Nguyen

(57) ABSTRACT

A surgical instrument which can be attached to a patient is described. The instrument includes an alignment guide having a distal end and a proximal end. A brace is attached toward the proximal end of the alignment guide for attaching the instrument to a limb of a patient. The brace comprises a pair of opposed members, each member being shaped to hold a respective bony part of the patient on either side of the patient. At least a part of the brace is made of a resilient material allowing the brace to grip the patient in use.

23 Claims, 4 Drawing Sheets

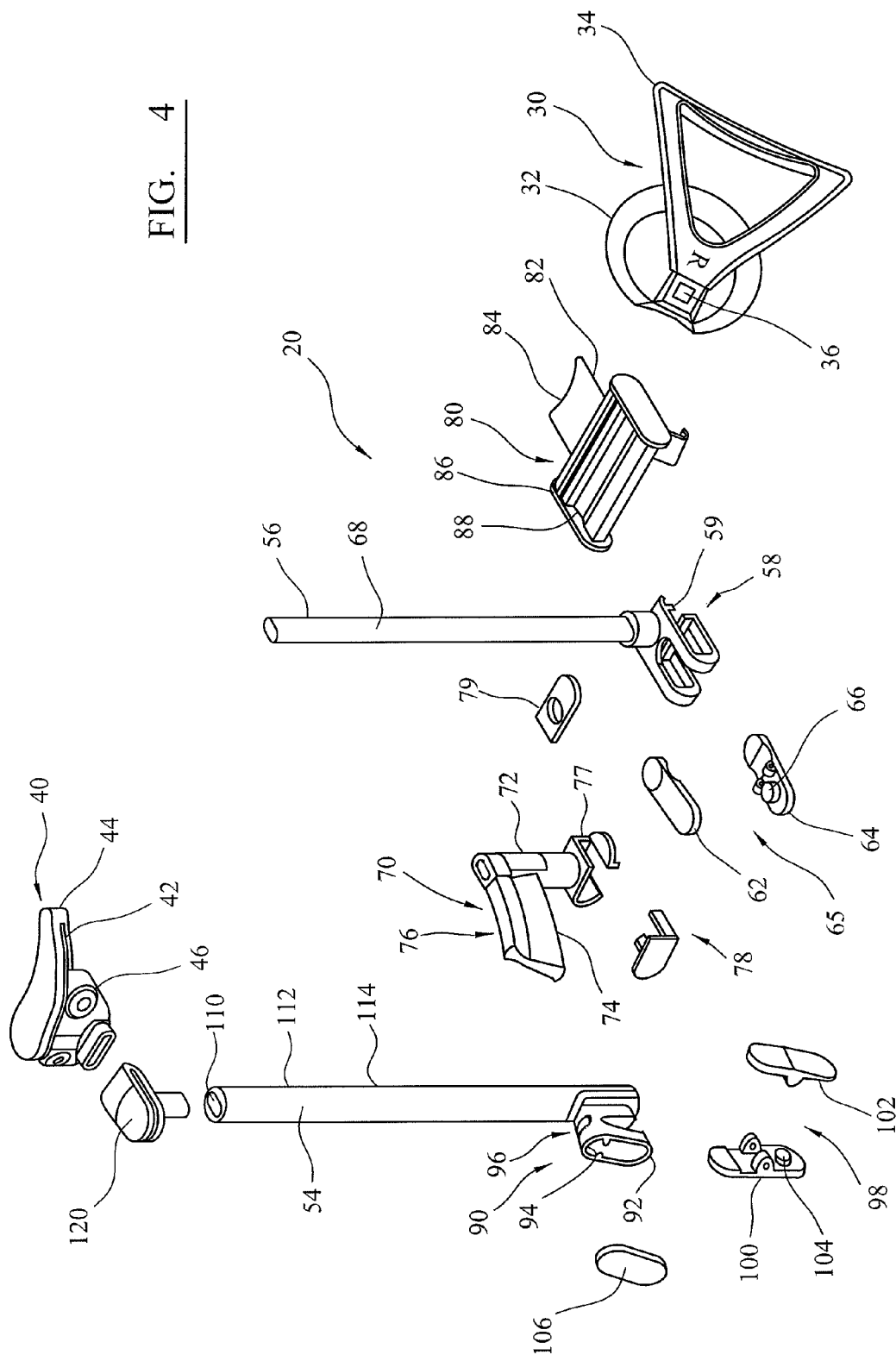

SURGICAL INSTRUMENT ATTACHMENT

CROSS REFERENCE TO RELATED APPLICATION

This application is a National Stage 35 U.S.C. 371 of International Patent Application PCT/GB2008/003182 filed Sep. 19, 2008.

The present invention relates to a surgical instrument, and in particular to a mechanism for attaching a surgical instrument to a patient.

BACKGROUND OF THE INVENTION

Various instruments and devices are used during orthopaedic arthroplasty procedures, such as, e.g., a knee arthroplasty procedure, to assist and guide the positioning of various instruments and devices used during the procedure.

For example, FIG. 1 shows a side view of a prior art external tibial alignment guide 10 attached to the lower leg of a patient which can be used during a knee arthroplasty procedure. The alignment guide 10 is used to position a tibial cutting block 12 against the tibial tubercle to perform a proximal tibial cut. The alignment guide includes an ankle clamp 14 by which the guide 10 is fixed distally to the patient's lower leg 16. The ankle clamp includes a block and a pair of clamps which engage around the ankle. The cutting block is attached to a telescopically extendable support member 18. The support 18 provides an external alignment guide by which the attached cutting block can be positioned and aligned relative to the longitudinal, inferior-superior axis of the tibia. That is, the support member can be aligned with the axis of the tibia.

The tibial resection position can be set using a stylus in combination with the cutting block 12 and once the height is selected, the cutting block can be pinned in place and the tibial cut performed.

However, the ankle clamp 14 gives rise to a number of problems. The ankle clamp can give rise to free, as well as accidental, translation and rotation, which will cause the alignment guide to move. Also, the ankle clamp can be difficult to use in practice as it requires manual manipulation and operation to clamp it around the patient. Further, during positioning around the patient, a users gloves can become caught in the clamp, which can delay the operation or require the gloves to be damaged and hence need replacing, causing further delays.

Hence, there is a need for a simple to use mechanism which allows instruments to be accurately and reliably attached to a patient.

BRIEF SUMMARY OF THE INVENTION

According to a first aspect of the present invention, there is provided a surgical instrument, comprising: a component having a distal end and a proximal end; and a brace attached toward the proximal end of the component for attaching the instrument to a limb of a patient, wherein the brace comprises a pair of opposed members, each member being shaped to hold a respective bony part of the patient on either side of the patient and wherein at least a part of the brace is made of a resilient material allowing the brace to grip the patient in use.

By making at least a part of the brace from a resilient material and shaping the members to hold bony parts of the patient, the instrument can be 'push fitted' in use to grip the patient and securely and reliably attach the instrument to a particular part of the patient. Hence, the instrument is easy to mount on a patient and resists movement relative to the patient as the brace grips the patient and the members lock to the bony parts of the patient's anatomy.

The brace can comprise more than two members. For example, the brace can comprise two or more pairs of opposed members. A different number of members can be provided on each side of the brace. For example a first side of the brace can have one member and the opposed side of the brace can have two members. It is possible to have more than two members on each side of the brace. The number and shape of members can be chosen to match or take advantage of the local bony anatomy of the patient at the position on the patient to which the brace is intended to be attached.

The component can be any type of surgical instrument or implement which needs to be attached to a patient in a preferred position. For example, the component can be an external alignment guide, such as a tibial alignment guide.

Either or each member can have a generally concave shape. The concave shape of the members can be adapted to receive respective bony parts of the patient in use.

Either or each member can have a generally closed form. For example, each member can be in the form of a cup or cap which can enclose the bony parts.

Either or each member can have a generally open form. That is, each member can define an aperture or hole therein through which the bony part of the patient can be palpated by the surgeon during attachment of the instrument. The hole or aperture can be wholly or partially enclosed by the member. For example, the member can be a closed loop of material or an open loop of material, having a generally U or C shape.

Either or each member can be shaped to extend at least partially around the bony part. Either or each member can be shaped to encircle the bony part.

Each member can have a generally rounded triangular or pear or tear drop shape.

Each member can be formed from a band of material. The band of material can be curved across its transverse dimension. This can facilitate push fitting the brace onto the patient.

Preferably the brace can be rotated through substantially 180°. This allows the same brace to be used on asymmetric body parts. The brace can be pivotally attached to the component or can be releasably attached to the component.

The brace can be asymmetric about a longitudinal axis of the instrument. This allows the brace to register with asymmetric bony parts.

Preferably each member is shaped to hold a malleolus. This allows the instrument to be attached to the leg of a patient by push fitting the brace onto the ankle.

The brace can be offset to a side of a longitudinal axis of the component. This allows the component to be automatically aligned with the body part by positioning the brace relative to the component to compensate for the position of the bony parts relative to an axis of the body part. For example, 60% of the brace can be to one side of the component and 40% of the brace can be to the other side of the component to allow the component to be positioned 60% from the lateral side and 40% from the medial side of the body part.

Preferably the brace is made from a plastics material. For example, the brace can be made from a biocompatible thermoplastic or thermoset polymer.

The whole or a part of either or each member can be made from a resilient material. The members can be joined by a part of the brace made from a resilient material. The whole of the brace can be made from a resilient material.

Suitable resilient materials include polymers, such as polyurethane, ABS, Nylon or polypropylene.

The brace can be made of a composite structure. The composite structure can include different classes or types of materials, such as metals and plastics. The members of the brace can be made of a plastics material and the members can be joined by a non-plastics part. The members can be joined by a metal part.

The materials properties and/or types of materials of the brace can be selected so that the brace is self centering on a range of different ankle sizes. The members can be made of different types of plastics. The members can have different stiffness or other mechanical properties.

According to a further aspect of the invention, there is provided a method for attaching a surgical instrument to a limb of a patient, the instrument comprising a component having a distal end and a proximal end and a brace attached toward the proximal end of the alignment guide, the brace comprising a pair of opposed members, and the method comprising: positioning the component adjacent the limb of the patient; and push fitting the brace onto the patient so that each member holds a respective bony part of the patient on either side of the patient so that the brace grips the patient.

The brace therefore provides an easy method for attaching a component to a limb of a patient at a preferred position and orientation without requiring significant manual manipulation or operation or wasted time.

BRIEF DESCRIPTION OF THE DRAWINGS

An embodiment of the invention will now be described, by way of example only, and with reference to the accompanying drawings, in which:

FIG. 4 shows an exploded perspective view of the alignment guide shown in FIG. 2.

DETAILED DESCRIPTION OF THE INVENTION

Figure 1:
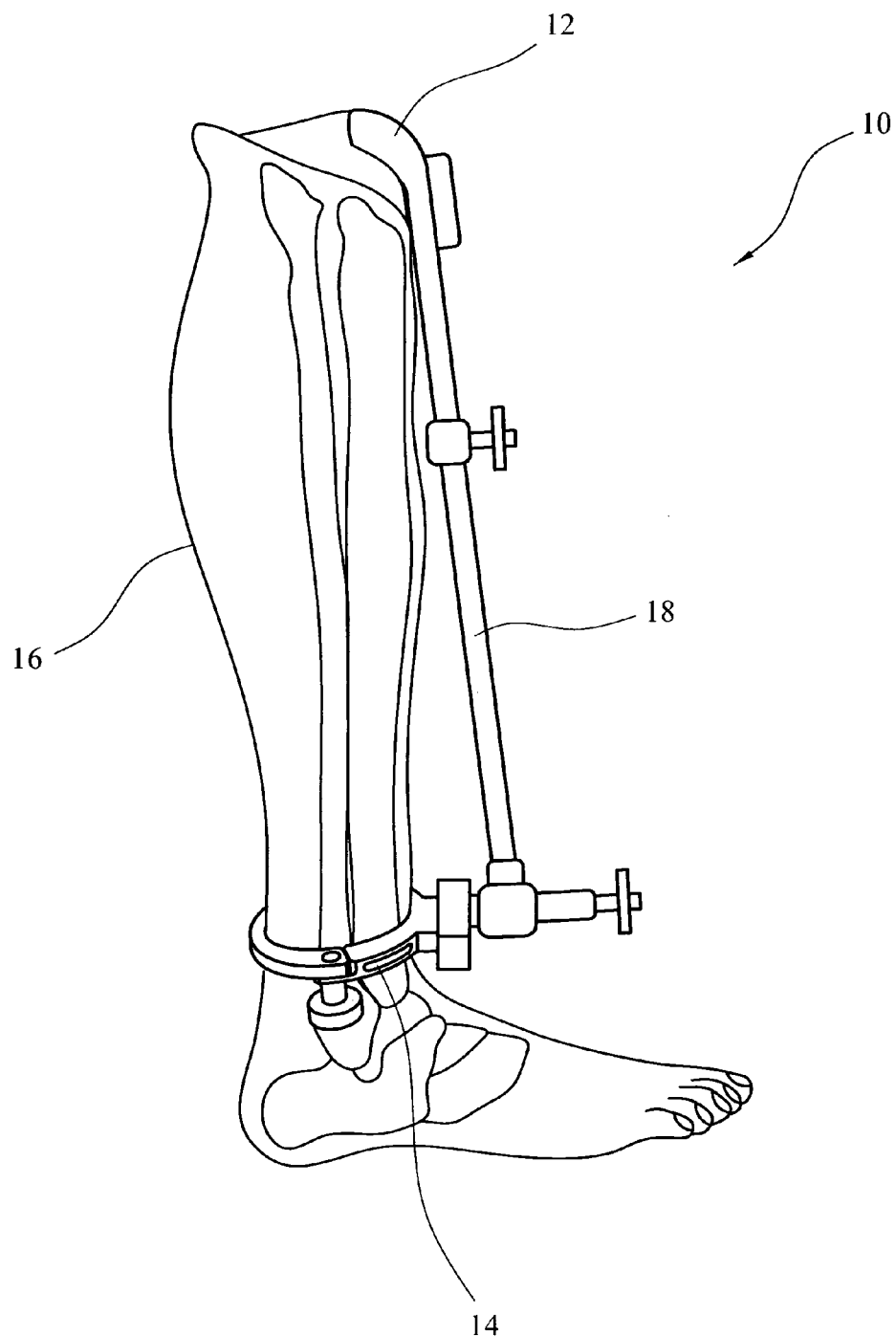
FIG. 1 shows a side view of a prior art external tibial alignment guide.

Similar items in different Figures share common reference numerals unless indicated otherwise.

Figure 2:
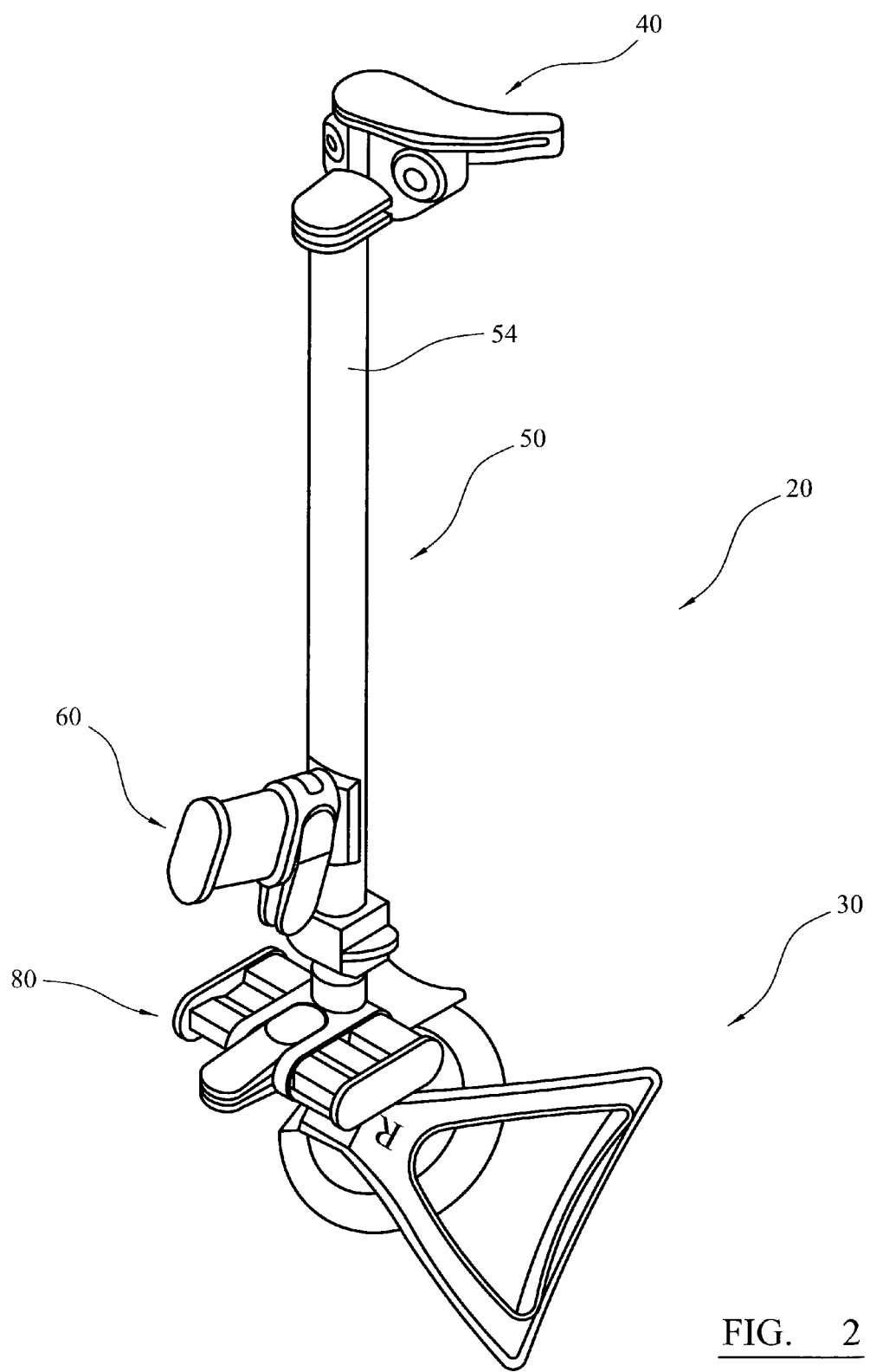
FIG. 2 shows a perspective view of an alignment guide including the invention.
Figure 3:
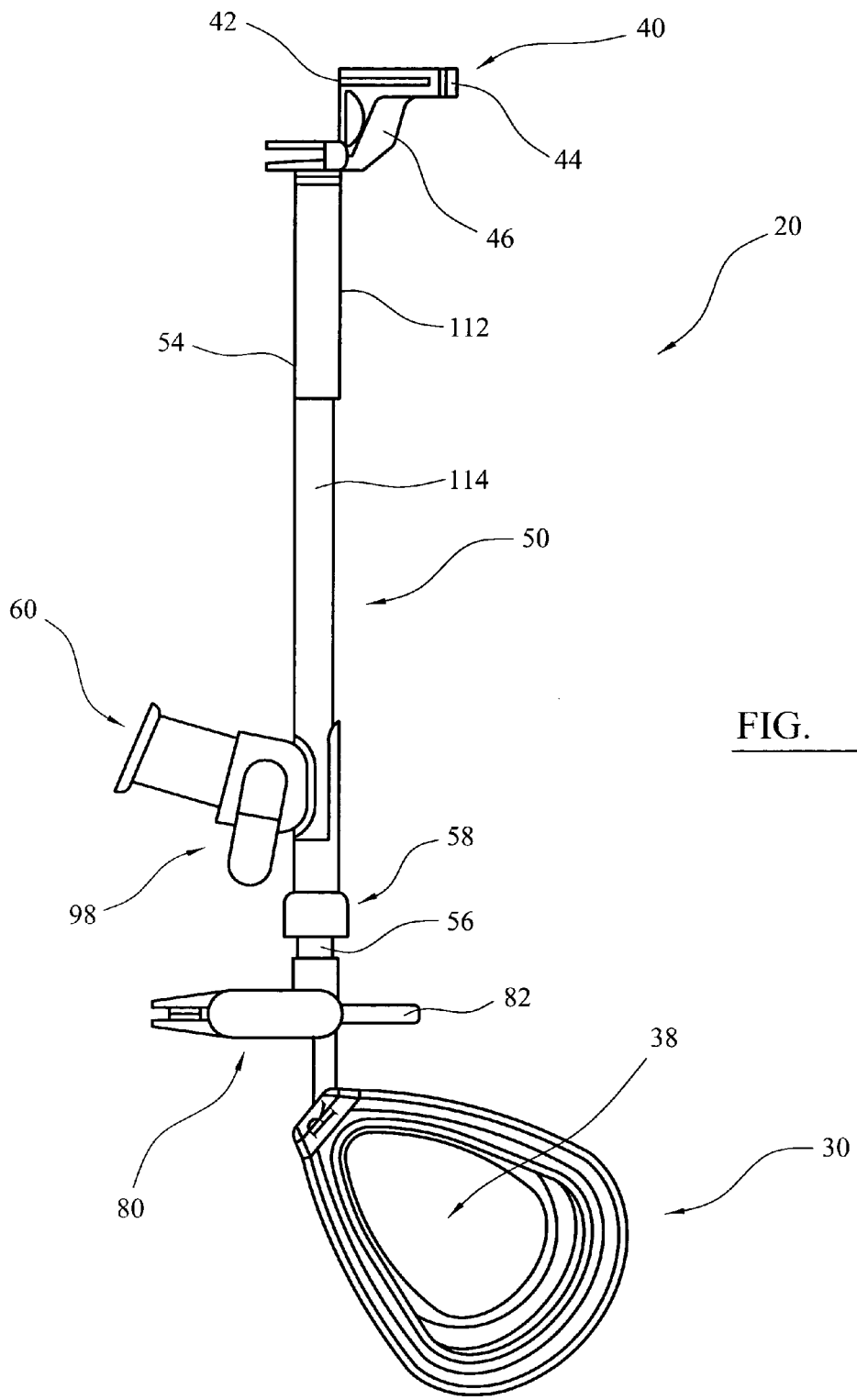
FIG. 3 shows a side elevation of the alignment guide shown in FIG. 2.

FIG. 2 shows a perspective view of an instrument 20 according to an embodiment of the present invention. FIG. 3 shows a side view of instrument 20 and FIG. 4 shows a perspective view of the exploded instrument, illustrating its constituent parts.

The instrument 20 generally includes a brace 30 toward a proximal end of the instrument for attaching the instrument to a patient as will be described in greater detail below. A component 40 is attached to a distal end of the instrument 20 and in the embodiment illustrated the component is in the form of a cutting guide. Instrument 20 also includes a further component 50 through which the cutting guide and brace are attached at respective ends. In the embodiment illustrated, the further component 50 is an external alignment guide. The alignment guide 50 includes a pivot mechanism 60 which allows a first, top portion of the alignment guide to pivot relative to a second, lower part of the alignment guide as will be described in greater detail below.

Brace 30 is attached to a base member 80 by a snap-fit mechanism which allows the brace to be releasably attached to the instrument. Base 80 has a generally planar member 82 extending from a rearward portion and presenting a curved edge 84. The shape and dimensions of member 82 are chosen to allow curved edge 84 to abut against a portion of the surface of the shin of a patient during use of the instrument. Base 80 includes a groove 86 and a curved trough 88 extending there across in a generally lateral or transverse direction.

The lower part or portion of the alignment guide component 56 includes a foot portion 58 having a generally U-shaped construction and adapted to engage with base 80 with rib 59 engaging trough 86 to allow sliding translation relative to base 80. A clamp assembly 65 includes first and second members 62, 64 and spring 66 which are attached to foot 58 by a metal pin and which can engage with trough 88 in use to prevent sliding.

Lower part 56 of the alignment guide includes a solid elongate member 68 extending from the foot 58 having a generally rectangular shape with a pair of opposed flat sides and a pair of opposed curved sides.

A first part 70 of the pivot mechanism 60 includes a generally hollow support 72 with a curved member 74 extending away therefrom. Curved member 74 bears a plurality of angular indicia 76 by an uppermost surface thereof. The first part 70 of the pivot mechanism includes a clip assembly 78 toward a lower end thereof. The clip assembly includes a generally hollow housing 77 having an aperture in a lower surface thereof and a clip plate 79 including a similar aperture. A spring component is also provided within the clip mechanism.

The member 68 of the lower portion 56 of the alignment guide passes through the apertures and hollow portions of the first part of the pivot assembly. With the clip plate 79 depressed against the action of the spring, the pivot assembly can be translated along the longitudinal axis of the member 68 to provide adjustment of the overall height of the instrument. The spring member acts against clip plate 79 to trap member 68 against the edges of the aperture in the clip plate to prevent translation and hence lock the height of the instrument.

The pivot assembly 60 includes a second part 90 provided toward an end of the second part 54 of the alignment guide. The second part of the pivot assembly 90 is in the form of a rounded, curved sleeve 92 having projections 94 on an inner portion thereof to mate with corresponding recesses in the curved member 74. An aperture 96 is provided in an upper surface enabling a one of the angular indicia 76 to be displayed, depending on the current position of the sleeve 92 along curved member 73. A clamp assembly 98 is also provided including first and second clamp drawers 100, 102 and a spring 104. Clamp assembly 98 is attached to sleeve 92 by a pin passing through the clamp drawers 100, 102 and into receiving apertures of the sleeve 92. An end stop plate 106 is also provided attached to a free end of the curve member 74 and sized to prevent free end of curve member 74 escaping from sleeve 92.

The second upper part 54 of the alignment guide has a generally circular cylindrical construction including a central aperture 110 running along its entire length. The aperture is shaped and dimensioned to receive member 68 so that upper part 54 can slide along the longitudinal axis of member 68. An upper region 112 has a closed cylindrical form while a lower region 114 has an open rear portion, as illustrated best in FIG. 3, having a generally C or U-shaped cross-section. The open portion is shaped in dimensions to allow member 68 to escape from within upper part 54 when upper part 54 is tilted relative to lower part 56.

Cutting block 40 is attached to the distal end of the alignment guide 50 by a spring clip 120 attached by a mail connector to which engages in the aperture 110 of upper part 54. Spring clip 120 allows various different components to be selectively attach to the instrument. In the illustrated embodiment the component is a cutting block 40 suitable for making a tibial cut during a knee arthroplasty procedure. Cutting block 40 includes a slot 42 passing through a generally plate-like curved upper portion 44 attached to a main body 46. Body 46 includes a plurality of coals for accepting a drill-bit to allow holes to be drilled in the patient's bone in use to accept pins for attaching the cutting guide 40 to the patient.

The curved member 64 of the pivot mechanism 60 has a radius of curvature centred on a point in the cutting block. Owing to this geometry, when the sleeve 92 is slid along curved member 74, the upper part 54 of the alignment guide tilts relative to the lower part 56, but the overall length of the instrument does not change, that is the height of at least a portion of the cutting block 40 above the brace does not significantly increase or decrease as the upper part of the alignment guide is effectively pivoting about a point located in the component. Therefore, the angle of the component 40 relative to the remainder of the instrument can be altered, without changing the overall length or height of the instrument. Therefore, in use, a surgeon can alter the angle of the cutting block 40 without having to then re-adjust the overall height of the instrument. The pivot mechanism is provided and configured so as to be able to use an arc (and therefore a proper angle) to set the posterior slope rather than a line (as occurs for prior art device) and to have a proximal pivoting reference to set the posterior slope which is independent of tibial length.

Instrument 20 includes brace 30 by which the instrument can be attached to and support on a patient. Although the embodiment illustrating the invention includes an alignment guide, it will be appreciated that in other embodiments, the brace 30 may be supporting other types of instruments or components relative to a patient's body. In this exemplary embodiment, instrument 20 is an external alignment guide including a tibial cutting block 40. The alignment guide 50 allows the cutting block to be aligned relative to the longitudinal axis of the tibia and also allows the height and angular position of the cutting block 40 to be adjusted to allow a tibial cut to be performed at a planned or preferred position and/or orientation.

The brace 30 includes a first 32 and a second 34 member on generally opposite sides of the brace 30. The members 32, 34 are attached to a common central or bridge portion 36 including an aperture part of a snap-fit fastener by which the brace 30 can be releasably attached to a co-operating part of base 80. Each member 32, 34 is in the form of a loop with an open hole or aperture defined thereby. The loop is formed from a ribbon or band material. The band material has a complex shape and curves in a number of directions. Firstly, the band of material is curved because its transverse dimension provide some spring force. Further, the band of material is curved to define a generally concave formation. Each loop is formed to define a generally pear or tear-dropped aperture 38 which is sized and shaped to accept a respective malleolus of the patient.

The entire brace component 30 is made from a resilient plastics material so that the brace is generally springy so that it can be push-fit onto the ankle of a patient so that the members 32, 34 encircle the malleoli and the resilient material of the brace causes the brace to securely grip the ankle of the patient and hold the instrument in place.

The brace can be made from a suitable plastics material such as various types of polymers, including polyurethane, ABS, Nylon or polypropylene. The plastics materials are selected to have a suitable elasticity and flexibility to be attached to and grip a range of different sizes of ankle in use. In other embodiments, the brace could be made from any suitable springy material, such as metals, alloys, composite materials, high yield stress metals, and hybrid metal and plastics.

As described above, the shapes of the members are adapted or configured so as to ensure that they wrap around the malleoli in use. The apertures in the brace allow the surgeon to feel the malleoli so that he is reassured of the correct positioning of the instrument. Dimensions of the apertures are designed to allow the brace to fit for around 95% of malleoli found generally in the population.

The shape of the malleoli together with the particular materials used are selected to provide the necessary fixation or grip force about the ankle so that the instrument can be push-fit attached to a patient. The instrument is at least partially self-locating as the spring force exerted by the resilient material of the brace causes the brace to lock onto the ankle in a generally unique position.

It will be appreciated that in other applications of the invention, the members will have different shapes and dimensions in order to capture other bony parts of features to which the brace is to be attached.

Also, the material of the brace is selected to provide sufficient flexibility and resilience of the brace to allow it to fit around 95% of ankle sizes present in the population.

The brace is asymmetric as the first and second members have different shapes and sizes to take into account the slightly differing anatomy of the malleoli on the left and right sides of the ankle. The instrument can be used on left hand and right hand ankles simply by removing the brace from the instrument, rotating the brace through 180 degrees and re-attaching the brace to the instrument. Therefore, a single instrument can be used on both the left hand side and right hand side ankles of a patient. Further, the brace is designed to automatically position the alignment guide with the tibia of a typical patient. Typically, the tibia is positioned approximately 60% from the lateral side and 40% from the medial side of the leg. Therefore, the brace is designed so that the alignment guide 50 is attached to the brace in a position approximately 60% from the lateral side and 40% from the medial side of the brace (wherein the medial and lateral sides of the brace are defined by the different shaped and sized members to accept the slightly different anatomy of the medial and lateral side malleolus). Hence, when the instrument is initially attached to a patient, the brace is automatically positioned at a 60/40 ratio in the medial-lateral direction of the patient so that the alignment guide is automatically approximately aligned with the tibia.

In other embodiments, the 60%-40% (or any other ratio) positioning of the brace can be also achieved by using two different materials for the same component. For example the brace can be made of two materials having different stiffness or mechanical properties, one for the medial and the other for the lateral portion. In this way, the brace can be self centering for any given ankle size.

The remainder of the parts of the instrument can be made of various plastics materials, such as ABS, polypropylene, polyurethane, polyethylene, polycarbonate and nylon, except for various spring and pin parts of the clamps and clips which are made of suitable bio-compatible metals. Further, the cutting guide 40 is typically made of a suitable bio-compatible metal, such as stainless steel or similar.

Use of the instrument will now be described. As explained above the invention is not limited to the particular external tibial alignment guide described, but can be used in other types of surgical instruments and similarly the method of use of the invention is not limited to specific instrument described.

Initially, the surgeon brings the instrument generally into alignment with the patient's lower leg, by generally aligning the longitudinal axis of the instrument with the longitudinal axis, i.e., in the inferior-superior direction, of the patient's lower leg. The brace is positioned anterior to and over the ankle, near to the malleoli. The surgeon can check whether the brace is in the correct orientation for the patient's ankle, and if not, then the brace can be removed, rotated by 180 and then re-attached to the instrument. The brace is pushed over the patient's ankle and the brace deforms to allow the ankle to enter into the mouth of the generally re-entrant or C-shaped cross sectional space defined by the members. The leading curved edges of the members rides over the malleoli until the brace is pushed sufficiently onto the ankle for the members to pass over to the posterior side of the malleoli and encircle the malleoli. Curved edge 84 of member 82 will be brought into abutment with a part of the front of the shin of the patient, so as to hold the alignment guide at a preferred position away from the tibia.

As the brace is made of a resilient material, the brace will automatically clamp about and securely grip the ankle. Also, as the holes in the members are shaped to accept the bony parts of the malleoli the brace will automatically settled about the malleoli and hence self-locate itself in a particular position. The grip exerted by the resilient material of the brace will also prevent the brace from moving significantly, unless sufficient force is applied to remove the brace by pulling it away from the ankle in a generally anterior direction. Further, as the alignment guide is located 60:40 along the width of the brace, the alignment guide is likely to be largely aligned with the middle of the tibia, absent any abnormal anatomy.

The surgeon, can then operate the base clamp 65 and slide the alignment guide in the medial-lateral direction, if required, in order to fine tune the positioning of the guide 50. The surgeon can also operate clip 79 in order to extend or reduce the length of the guide, if required, so as to position the cutting block at the correct height relative to the distal part of the tibia for making the tibial cut. The surgeon can also tilt the upper part of the alignment guide to change the cutting angle of the cutting block by operating pivot mechanism clamp 98, and pushing the upper part of the guide and cutting block toward the tibia. The surgeon can view the current degree of tilt displayed through aperture 96 to determine when the desired degree of tilt has been achieved. As the curved member has a radius of curvature which terminates generally in the upper plate of cutting block, the overall length of the guide, that is the separation between the cutting guide slot of the cutting block and the brace does not substantially change, when the upper part is tilted and so the height of the cutting block relative to the tibia does not need changing.

The cutting block can then be pinned in place. The spring clip 120 can then be operated to release the cutting block and the surgeon can pull on the instrument to release the brace from around the malleoli. Hence, the surgeon can more easily attach and release the instrument using the brace. The instrument also provides greater adjustability and ease of use.

The invention claimed is:

1. A surgical instrument for attachment to a limb of a patient, the limb having bony parts, the surgical instrument comprising:
   an alignment guide having a longitudinal axis, a distal end and a proximal end; and
   a brace attached toward the proximal end of the alignment guide for attachment to the limb, the brace including a first member extending away from the alignment guide at a first location in a first direction, and a second member extending away from the alignment guide at a second location in a second direction, the first location being on one side of the longitudinal axis and the second location being on the other side of the longitudinal axis, each member being shaped to hold a different respective bony part of the limb located on either side of the limb, and wherein at least a part of the brace is made of a resilient material and wherein the first member and the second member are each in the form of a loop that defines an aperture.

2. The instrument of claim 1, wherein each member has a generally concave shape adapted to receive the respective bony parts of the limb.

3. The instrument of claim 1, wherein each member has a generally closed form.

4. The instrument of claim 1, wherein each member is shaped to extend at least partially around the bony part.

5. The instrument of claim 4, wherein each member is shaped to encircle the bony part.

6. The instrument of claim 1, wherein each member is formed from a band which is curved across its transverse dimension.

7. The instrument of claim 1, wherein each loop of the first and second members has a triangular shape.

8. The instrument of claim 1, wherein the first direction and the second direction are substantially parallel.

9. The instrument of claim 1, wherein the brace can be rotated through substantially 180°.

10. The instrument of claim 1, wherein the brace is asymmetric about a longitudinal axis of the instrument.

11. The instrument of claim 1, wherein each member is shaped to surround a malleolus.

12. The instrument of claim 1, wherein the brace is offset to a side of a longitudinal axis of the alignment guide.

13. The instrument of claim 1, wherein the brace is made from a plastics material.

14. The instrument of claim 1 wherein the brace is made of a composite structure.

15. The instrument of claim 14, wherein the members of the brace are made of a plastics material and the members are joined by a metal part.

16. The instrument of claim 1, wherein the brace is configured such that the brace is self-centering on a range of different ankle sizes.

17. A method for attaching a surgical instrument to a limb of a patient, the instrument comprising an alignment guide having a distal end and a proximal end and a brace attached toward the proximal end of the alignment guide, the brace comprising a pair of opposed members, each member being shaped to surround a malleoli located on either side of the limb the method comprising the steps of:
   positioning the alignment guide adjacent the limb of the patient; and
   positioning the brace so that each member surrounds a respective malleoli of the patient located on either side of the limb.

18. A surgical instrument, comprising:
   an alignment guide having a distal end and a proximal end; and
   a brace attached toward the proximal end of the alignment guide for attaching the instrument to a limb of a patient, wherein the brace comprises a pair of opposed members, each member being shaped to hold a respective bony part of the patient on either side of the patient and wherein at least a part of the brace is made of a resilient material allowing the brace to grip the patient in use, wherein each member has a generally rounded triangular shape.

19. A surgical instrument for attachment to a limb of a patient, the limb having bony parts, the surgical instrument comprising:
- an alignment guide having a longitudinal axis, a distal end and a proximal end; and
- a brace attached toward the proximal end of the alignment guide for attachment to the limb, the brace including a first member extending away from the alignment guide at a first location in a first direction, and a second member extending away from the alignment guide at a second location in a second direction, the first location being on one side of the longitudinal axis and the second location being on the other side of the longitudinal axis, each member being shaped to surround a malleoli located on either side of the limb.

20. The instrument of claim 19, wherein the first member and the second member are each in the form of a loop that defines an aperture.

21. The instrument of claim 20, wherein each loop of the first and second members has a triangular shape.

22. The instrument of claim 19, wherein at least a part of the brace is made of a resilient material.

23. The instrument of claim 19, wherein the first member and the second member are each in the form of a loop that defines an aperture.

* * * * *